US006300139B1

(12) United States Patent
Alvarez

(10) Patent No.: US 6,300,139 B1
(45) Date of Patent: Oct. 9, 2001

(54) FTCD ANTIGEN

(75) Inventor: Fernando Alvarez, Town of Mount Royal (CA)

(73) Assignee: Hôpital Sainte-Justine, Montréal (CA)

( * ) Notice: Subject to any disclaimer, the term of this patent is extended or adjusted under 35 U.S.C. 154(b) by 0 days.

(21) Appl. No.: 09/373,750

(22) Filed: Aug. 13, 1999

Related U.S. Application Data

(63) Continuation-in-part of application No. PCT/CA98/00116, filed on Feb. 13, 1998.
(60) Provisional application No. 60/038,021, filed on Feb. 14, 1997.

(51) Int. Cl.[7] .......................... G01N 33/564; C07H 21/04
(52) U.S. Cl. .......................... 436/506; 436/518; 436/820; 435/7.4; 435/7.92; 435/7.95; 536/23.2; 536/23.5
(58) Field of Search ................... 536/23.2, 23.5; 435/7.4, 7.92, 7.95; 436/506, 518, 820

(56) References Cited

PUBLICATIONS

Murley et al., The Nucleotide Sequence of Porcine Formiminotransferase Cyclodeaminase, Expression and Purification from *Escherichia coli*. The Journal of Biological Chemistry 268(30):22820–22824, 1993.*

Asuaf et al., Characterization of the Liver Cytosol Antigen Type 1 Reacting with Autoantibodies in Chronic Active Hepatitis. Hepatology 16(4):892–898, 1992.*

Solans et al., Cloning and characterization of human FTCD on 21q22.3, a candidate gene for glutamate formiminotransferase deficiency. Cytogenetics and Cell Genetics 88:43–49, 2000.*

* cited by examiner

*Primary Examiner*—Donna C. Wortman
(74) *Attorney, Agent, or Firm*—Swabey Ogilvy Renault; France Côte

(57) ABSTRACT

The present invention relates to FTCD antigen which is liver specific to serve as a diagnostic tool for Autoimmune Hepatitis type II. There is provided a human liver specific FTCD antigen recognized by LC1 antibodies which essentially consists in the amino acid sequence of SEQ ID NOS:3 and 4 or variants thereof which are recognized by LC1 antibodies. There is also disclosed a method of diagnosis of Autoimmune Hepatitis (AIH) type II disease in a patient biological sample, which comprises the steps of: a) subjecting a Western Blot having bound thereto an FTCD antigen of the present invention with the patient biological sample; and b) detecting the presence of LC1 antibodies in the sample; whereby the presence of LC1 antibodies is indicative of AIH type II disease.

5 Claims, 7 Drawing Sheets

```
FTCD PIG   CCGCCCTTCCACGCGGGCCTCAGCCAAGCTGACCTTCGCTGTGGTGACGCTGACGCCCGGGCC   1245
                ||||||||||  || ||  || |||||||||||||||| ||||| ||||| ||||| |||||
LCHC1      CCGCCCTTCCGCGAGGCTTCGGCCAAGCTAACCACGCGTGGTGGATGCCGACGCCGAGGCC

FTCD PIG   TTCGAGGCCTACCTGAAAGCGATGAAGCTGCCCAAGGACACACCCGAGGACAAGGACAGG   1305
                ||  ||||||||||||| || ||||| ||||||||||| || ||||||||| ||||||
LCHC1      TTCACCGCCTACCTGGAAGCAATGAAGCTCCCCAAGAACACACCTGAGGAAAAGGACAGG

FTCD PIG   CGTGCGGCTGCCCTGCAGGAGGGGCTGAGGCAGGCAGTGGCTGTGTGCCCCTGGCGCTGGCG   1365
                || ||||||||||||||| || || || |||||||||| ||| | | |||| ||||||||
LCHC1      CGCACGGCGGCCCTACAGGAGGTCTGAGGCAGTCTCTGTGCCGCTCTGTGCCGCTGACGCTGGCG

FTCD PIG   GAGACGGTGGCCTCGCTGTGGCCGGCACTGCAGGAGCTGCAGGCCCCTGTGTGGGAACCTGGCC   1425
                ||||||||||||||||||||||| |||| ||||||||||| ||||||||| |||||||||||
LCHC1      GAGACGGTGGCCTCGCTGTGGCCGGTGCTGCAGGAACTGGCCCCGTGTGGGAACCTGGCC

FTCD PIG   TGCCGATCTGACCTGAGACCTCCAGGTGCGGCCAAGGCCCCTGAGAGACAGGTGTGTTTGGTGCCTAT   1485
                |||| | |||| || ||  |||||||||||||||||||| |||||| ||||||||||||||||
LCHC1      TGCCGGTCAGACCTCCAGGTGCGGCCAAAGCCCCTGAGATGGGCGTGTTTGGCGCATAT

FTCD PIG   TTCAACGTGCTCATCAACCTGAAAGATGTCACGGATGACGCGTTTAAGGCCCAGGTCCGT   1545
                |||||||||||||||||||||   ||  | |  ||  || ||| |||||||| |||||||||
LCHC1      TTCAACGTGCTCATCAACCTGAGGGACATCACAGAGGCATTTAAGGACCAGATCCAC
```

FIG. 3A

```
FTCD PIG    CAGGCGCATCTCCAGCCTCTCCTGCAGGAAGCCAAGACCCCAGGCGGCACTGGTGCTGGACCGG   1605
            ||||  ||  ||||||||||||||||||||||||||||  |||||||  ||||||||||
LCHC1       CATCGTGTTTCCAGCCTCTCCTGCAGGAAGCCAAGACCCAGGCTGCACTGGTGCTGGACTGC

FTCD PIG    CTGGAGGCCCGGCAGGGCGTGACGGCTGGAGGGGCACCTCCCCTGGACCCTGTCCTTGCTGA   1665
            |||||||  |||||||||||||||  |||
LCHC1       TTGGAGACCCGGCAGGAGTGACGAAACCCCAGGACACAGCAGGACCTTGACGCTGGAAGG

FTCD PIG    GGCCCCTCACTGTCTGGACGACAGGGTGGCCTCCAGACCTGTCCTGGGGCCCGGAGAG      1725
LCHC1       ATAGCCTCGCTTCCCAGGTGCAGTCCCGGCAGGTCTGGACAGTTCCACAGAGCACGGTA

FTCD PIG    GGCAGGGAGTGGGGGCAAGGAAGGGGGCTCTGGGGCAGTGGCATCACCTTCTGTCA        1785
LCHC1       CTGGCCCCTGTCCCTCAGTTCCCACCCTTCAACCAGTGGCTCCTGGAGACTTTCCTC

FTCD PIG    CCTGTGGCTTCCAGTAAAGTGATGACACCAAAAAAAAAAAAAAAAAAAA               1838
LCHC1       CCTGCCCTCAGTCCCCAGCCCTGCCCAGCCTCCTGTCTCTCCAGAGAAGTTCTCATTAAAAAA
```

FIG. 3B

```
FTCD pig   PPFHAASAKLTSLVDADARAFEAYLKAMKLPKDTPEDKDRRAAALQEGLRQAVAVPLALA
           ||||| ||||||||||||||| |||||||| |||| |||| |||||||||||| |||| ||
LCHC1      PPFREASAKLTTLVDADAEAFTAYLEAMRLPKNTPEEKDRRTAALQEGLRRAVSVPLTLA   455

FTCD pig   ETVASLWPALQELALCGNLACRSDLQVAAKALETGVFGAYFNVLINLKDVTDDAFKAQVR
           |||||||||||||| |||||||||||||||||||| ||||||||||||| ||| |||
LCHC1      ETVASLWPALQELARCGNLACRSDLQVAAKALEMGVFGAYFNVLINLRDITDEAFKDQIH   515

FTCD pig   QRISSLLQEAKTQAALVLDRLEARQA
            | ||||||||||||||| ||| ||
LCHC1      HRVSSLLQEAKTQAALVLDCLETRQE                                     545
```

FIG. 4

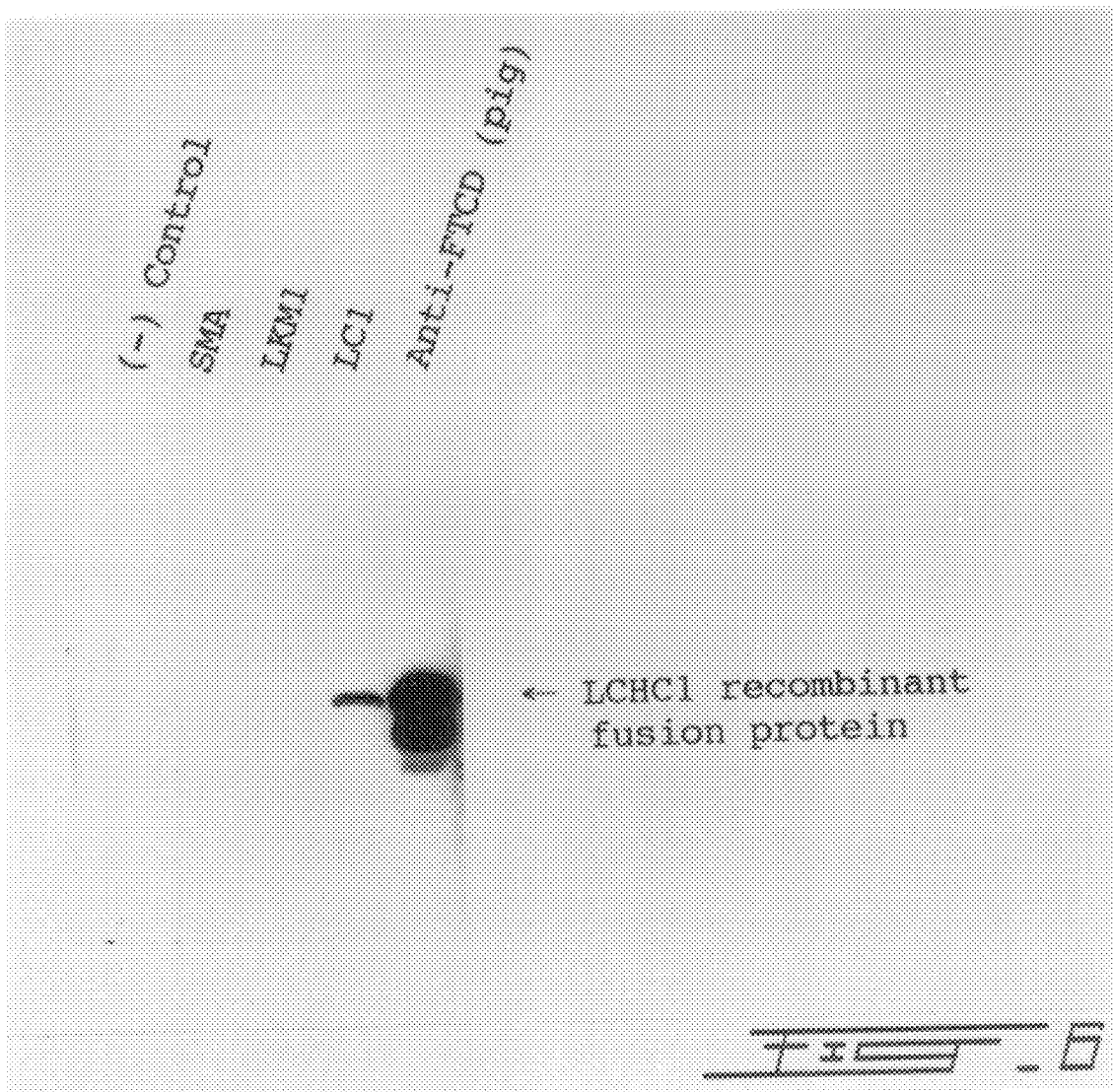

FTCD ANTIGEN

This application is a continuation-in-part of PCT/CA98/00116, filed Feb. 13, 1998, and which designated the United States, and claims the benefit of U.S. Provisional Appliction No. 60/038,021, filed Feb. 14, 1997.

BACKGROUND OF THE INVENTION (a) Field of the Invention

The invention relates to formiminotransferase cyclodeaminase (FTCD) antigen which is liver specific to serve as a diagnostic tool for Autoimmune Hepatitis type II.

(b) Description of Prior Art

Autoimmune Hepatitis (AIH) is a disorder of unknown etiology responsible for a progressive destruction of the hepatic parenchyma with a high mortality if left untreated (Johnson P. J. et al., 1993, Meeting Report: International Autoimmune Hepatitis Group, Hepatology, 18:998–1005). One of the characteristics of this disease is the presence of circulating autoantibodies in almost 90% of patients' sera. Clinical and serological differences between patients have lead to the classification of AIH into two types. Type 1 is characterized by the presence of anti-smooth muscle (SMA) and/or anti-nuclear antibodies (ANA) in patients' sera, while sera from Type II patients show anti-liver kidney microsomal antibodies type 1 (LKM1) (Homberg J. C. et al., 1987, Hepatology, 7:1333–1339; Maggiore G. et al., 1993, J. Pediatr. Gastroenterol Nutr., 17:376–381). Recently, a new serological marker, anti-liver cytosol type I antibodies (LC1), was identified in 30% of patients with an AIH type II. In addition, LC1 proved to be the only serological marker in 10% of patients tested (Martini E. et al., 1988, Hepatology, 8:1662–1666). This new organ specific autoantibody is a great contribution to the diagnosis of AIH, especially in patients considered so far as seronegative.

Recently, it was found that the liver cytosol recognized by LC1 had a molecular weight of 62 kDa in human liver and of 58 kDa in rat liver (Abuaf N. et al., 1992, Hepatology, 16:892–898). Furthermore, the authors concluded that LC1 is a more specific marker of autoimmune hepatitis type II than the LKM1 (Abuaf N. et al., 1992, Hepatology, 16:892–898).

It would be highly desirable to be provided with a diagnostic tool specific for Autoimmune Hepatitis type II.

SUMMARY OF THE INVENTION

One aim of the present invention is to provide a diagnostic tool specific for Autoimmune Hepatitis type II which would enable a clinician to distinguish AIH from HCV.

In accordance with the present invention there is provided the human liver FTCD as the specific antigen recognized by LC1 antibodies.

In accordance with the present invention there is provided a human liver specific FTCD antigen recognized by LC1 antibodies which essentially consists in the amino acid sequence of SEQ ID NOS:3 and 4 or variants thereof which are recognized by LC1 antibodies.

In accordance with the present invention there is provided such a human FTCD antigen which is encoded by a DNA sequence of SEQ ID NOS:1 and 2 and variants thereof which codes for an antigen recognized by LC1 antibodies.

In accordance with the present invention there is provided a method of diagnosis of Autoimmune Hepatitis (AIH) type II disease in a patient biological sample, which comprises the steps of:

a) subjecting a Western Blot having bound thereto an FTCD antigen of the present invention with the patient biological sample; and b) detecting the presence of LC1 antibodies in the sample; whereby the presence of LC1 antibodies is indicative of AIH type II disease.

In accordance with the present invention there is provided an ELISA method of diagnosis of Autoimmune Hepatitis (AIH) type II disease in a patient biological sample, which comprises the steps of:

a) subjecting an ELISA plate having bound thereto an FTCD antigen of the present invention with the patient biological sample; and b) detecting the presence of LC1 antibodies in the sample using rabbit anti-human IgG antibodies; whereby the presence of LC1 antibodies is indicative of AIH type II disease.

The term "variants thereof" is intended to mean any variation in the amino acid sequence of SEQ ID NOS:3 and 4 resulting in a peptide which is still recognized by LC1 antibodies or any variation in the DNA sequence of SEQ ID NOS:1 and 2 coding for a peptide which is still recognized by LC1 antibodies.

The term "molecular mimicry" is intended to mean any homology between the sequence of LCHCl and any other known sequence. LCHCl is a liver cytosol human clone 1 is the cDNA coding for human FTCD that we have identify in a cDNA library from HepG2 cells which codes for about 150 amino acids of the FTCD COOH-terminal region.

BRIEF DESCRIPTION OF THE DRAWINGS

FIGS. 3A and 3B illustrates the DNA sequences of FTCD pig (SEQ ID NO:1) and LCHCl (SEQ ID NO:2) antigens;

FIG. 4 illustrates the amino acid sequences of FTCD pig (SEQ ID NO:3) and LCHCl (SEQ ID NO:4) antigens;

FIG. 6 illustrates a Western blot of the LCHCl recombinant fusion protein.

DETAILED DESCRIPTION OF THE INVENTION

Figure 1A:
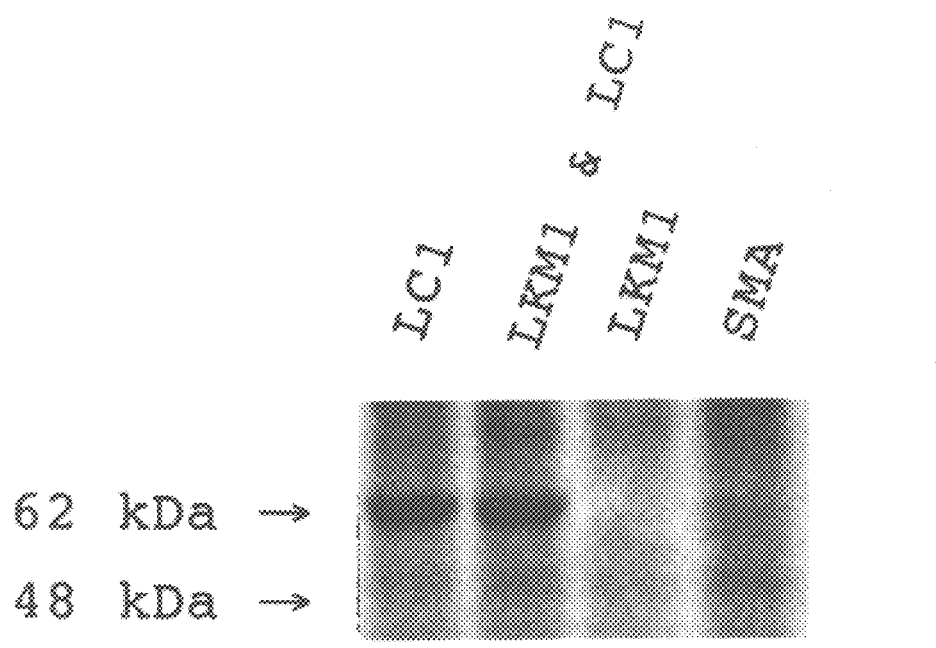
FIGS. 1A and 1B show that the human hepatoma HepG2 cell line express the LC1 antigen.

In accordance with the present invention there is provided the identification, through different methods, of the human liver FTCD as the specific antigen recognized by LC1 antibodies. These findings will permit not only a characterization of the immune response and a search for molecular mimicry and its pathogenic relevance but also the development of more specific diagnostic tests.

Materials

Restriction enzymes were obtained from Pharmacia LKB Biotechnology Inc. Boehringer Mannheim or Life technologies. Nitrocellulose and nylon membranes used for screening, immuno and Northern blotting were from Amersham Corp. Both the enzyme and reagent used for sequencing DNA were from United States Biochemical Corp. The factor, maltose-resin and anti-MBP control antiserum were bought from New England Biolabs. The enzyme and reagent for the oligolabeling were from Pharmacia Biotech.

HepG2 Cells Labeling and Immunoprecipitation

HepG2 cells were obtained from American Type Culture Collection (ATCC, 12301 Parklawn Drive, Rockville, Md. 20852 USA, under deposit accession number ATCC 8065-HB), and maintained in minimum essential medium (MEM) containing Earle's salts, non-essential amino acids, glutamine, 10% fetal calf serum and streptomycin/penicillin. Cultures were made in 6 well plates and maintained at 37° C. in an atmosphere with 5% $CO_2$. For labeling, cells (approximately $1 \times 10^6$) were rinsed with PBS and incubated for 30 minutes at 37° C. with MEM without cysteine. Later, this media was replaced by fresh MEM with 200 $\mu$Ci/ml of $S^{35}$ cysteine and cells maintained at 37° C. for another 30 minutes. Then the radioactive media was replaced by MEM with unlabeled cysteine at 500 times higher concentrations than the radioactive amino acid. Incubation was continued for 90 minutes at 37° C. The cells were washed and resuspended in 500 $\mu$l of the following buffer: 10 mM NaCl, 10 mM Tris-HCl pH 7.4, 1.5 mM $MgCl_2$, 1% sodium deoxycholate, 1% NONIDET™ P-40. Immunoprecipitation was then carried out with 200 $\mu$l of HepG2 cell suspension diluted with 4 volumes of 190 mM NaCl, 50 mM Tris-HCl pH 7.4, 6 mM EDTA and 2.5% TRITON™ X-100. Ten (10) $\mu$l of serum were added to the immunoprecipitation test tube, and the samples were incubated at 4° C. overnight. Sera used in the immunoprecipitation reaction were those positive by ELISA at titers between 1:400 and 1:800. Immunocomplexes were precipitated by adding Protein A SEPHAROSE™ (20 $\mu$l of swollen beads) to the solution and incubating 2 hours at room temperature. The immunoprecipitate was analyzed by Sodium dodecyl sulfate-polyacrylamide gel electrophoresis (SDS-PAGE).

RNA Preparation and Analysis

The total RNA was prepared from human liver (1 g) and HepG2 cells ($2 \times 10^7$) using the single step method described below (Chomczynski P. and Sacchi N., 1987, *Anal. Biochem.* 162:156–159). The cells are washed with ice-cold PBS and collected by centrifugation (5 min. at 1000 RPM). The collected cells are resuspended in 375 $\mu$l ice-cold lysis buffer, followed by being incubated on ice for 5 min. and then transferred to microcentrifuge tube (spin 2 min. at 4° C.). The supernatant fluid is removed to clean the tube containing 4 $\mu$l of 20% SDS and mixed. An amount of about 2.5 $\mu$l of 20 mg/ml proteinase K is added and followed by an incubation of about 15 min. at 37° C. An extract is effected with 400 $\mu$l phenol/chloroform/isoamyl alcohol by recovering the aqueous (upper) phase. Repeat phenol/chloroform/isoamyl alcohol extraction. An extract is performed with 400 $\mu$l chloroform/isoamyl alcohol and the aqueous phase is recovered. Forty (40) $\mu$l of 3 M sodium acetate, pH 5.2 and 1 ml ethanol are added. This is followed by a precipitating step of about 15 to 30 min. on ice or overnight at −20° C. The RNA is collected by centrifugation for 15 min. at 4° C. The pellet are rinsed with 1 ml of 75% ethanol/25% 0.1M sodium acetate, pH 5.2 and then dry them. Redissolve pellets in 100 $\mu$l of water and dilute 10 $\mu$l in 1 ml of water to determine the $A_{260}$ and $A_{280}$. The RNA may be stored at −70° C.

The total RNA was then analyzed by Northern blotting (Ausubel F. M., 1995, et al., *Current protocols in molecular biology*, (John Wiley & Sons, Inc.) 4.9.2–4.9.8 (eds)). Five (5) $\mu$g of total RNA from human liver and HepG2 cells was loaded on a 1% agarose-formaldehyde gel, then transferred onto a nylon membrane. The membranes were probed with the P450 2D6 cDNA and the cDNA fragment of LCHCl $^{32}$P-labeled using the random priming method (Feinberg A. P. and Vogelstein B., 1983, Anal. Biochem. 132,6). Random oligonucleotide-primed synthesis is an alternative to nick translation for producing uniformly radioactive DNA of high specific activity. To carry out the labeling procedure, the DNA is cleaved with a restriction endonuclease, and, if desired, purify the DNA fragment containing the sequence of interest by gel electrophoresis. The resulting linear DNA molecules are denatured by boiling, annealed to random-sequence oligodeoxynucleotides (typically six bases in length); and then are incubated with the Klenow fragment in the presence of dNTPs. In this way, the hexanucleotides prime the DNA of interest at various positions along the template, and are extended to generate double-stranded DNA that is uniformly labeled on both strands.

The membranes were prehybridized for 3 hours at 42° C. in 5×SSC, 5×Denhardt, 50% formamide, 1% SDS, and hybridized in the same solution plus $1 \times 10^6$ CPM/ml of labeled probe overnight at 42° C. The membranes were washed as described and exposed for 1 week for autoradiography.

Isolation and Characterization of cDNA Clones

To isolate the cDNA encoding for the LC1 antigen, a λgt11 HepG2 cDNA expression library (Clontech) was used. Sera from two patients with anti-LC1 antibody but negative for LKM1 as confirmed by immuno blotting were used to screen the library. A total of $5.6 \times 10^6$ recombinants were screened using standard procedure (Sambrook J. et al., 1989, Molecular Cloning: A laboratory manual, Cold Spring Harbor Laboratory, 2:12.16–12.20). The filters were incubated overnight at 4° C. in a 1/1000 dilution of each sera and the putative positive clones were plaque-purified. 6 clones were identified as potential positives, to confirm this, fusion proteins were prepared from our recombinant phages. Recombinant phage lysogens were identified and grew overnight at 32° C. in LB/ampicillin with good aeration. Next the temperature was raised to 42° C. for 30 minutes, 10 mM isopropyl-l-thio-β-d-galactoside (IPTG) was added and the culture incubated at 37° C. for two hours. The cultures were centrifuged and resuspended in SDS-gel loading buffer and boiled for 5 minutes. The resulting proteins were then analyzed by immuno blotting. Two of the 6 clones were found to be positives.

cDNA Subcloning and Sequencing

The restricted fragment of the two LCHCl clones were subcloned into the EcoRl site of pBluescript sk+ cloning vector using standard molecular biology techniques (Sambrook J. et al., 1989, Molecular Cloning: A laboratory manual, Cold Spring Harbor Laboratory, 3:f1–f11). The cDNAs were then sequenced using the dideoxy-chain termination method (Sanger F. et al., 1977, *Proc. Nat. Acad. Sci.*, 74:5463–5467). Both the M13–20 oligonucleotide primer and internal primers (Immunocorp Inc.) were used to sequence both clone.

Expression and Purification of the LCHCl Fusion

The EcoR1 fragment of the λgt11 clone was sub-cloned into the EcoR1 site of the pMa1 vector (New England Biolabs) conserving the reading frame of λgt11. The resulting construction was then transformed into the TB1 strain using standard method (Sambrook et al., 1989). Briefly, the fusion protein was expressed as described (Ausubel, Brent et al (eds)). A 100 ml LB/ampicillin culture was grown to $2 \times 10^8$ cells/ml and then induced with IPTG at 0.3 mM for 90 minutes at 37° C. with shaking. The bacteria were then sonicated in 5 mL of column buffer: 20 mM Tris-HCl pH 7.4, 0.2 M NaCl, 1 mM EDTA. This solution was incubated with 1 mL of maltose resin (New England Biolabs) overnight at 4° C. with gentle shaking. The maltose resin was loaded onto a 0.8×4 cm chromatography column (Bio-Rad Laboratories), the column was washed with 12 column volumes of column buffer, and the protein eluted with column buffer/10 mM maltose. The different fractions along with the cells lysate were electrophoresed on SDS-PAGE to detect the fusion protein.

Mice Immunization and Antibody Purification

Three C57BL6 female mice at 6 weeks of age were injected intraperitoneally with 50 µg of the purified protein coded by LCHCl emulsified in 200 µl of Freunds complete adjuvant. Three weeks later the mice were boosted IP with 50 µg of the same antigen emulsified in 200 µl of incomplete Freunds adjuvant. One week later the mice were bled and the sera were tested by immuno blotting. For antibody purification a total of 50 µg was coupled to activated 6-aminohexanoic acid-SEPHAROSE™ 4B (Sigma chemical company). The washed resin was loaded onto a 0.8×4 cm chromatography column (Bio-Rad laboratories), 50 µl of LC1 positive serum diluted in 1 ml of PBS was applied to the column. The column was then washed with 10 ml of PBS and the affinity purified antibody was eluted with 0.05 M glycine, 0.15 M NaCl, titrated with HCl to pH 2.3. The purified antibodies were then tested against human liver cytosol subcellular fraction by immunoblotting.

Indirect Immunofluorescence

HepG2 cells on cover-slips were fixed with 4% paraformaldehyde in PBS. Fixed cells were treated with 0.1% Triton X-100 in PBS to allow the passage of antibodies into the cells. Treated cells were incubated with 0.2% gelatin in PBS during 30 minutes to block non-specific binding sites. First antibodies used in the indirect immunofluorescence technique were: 1) LC1 positive patient sera; 2) anti-LHCHl affinity purified antibody; 3) anti-LHCHl mouse serum; 4) anti-pig FTCD serum; 5) anti-nuclear antibody (positive control); and normal human serum (negative control); at dilutions between 1:50 and 1:2000. Second antibodies used were: 1) anti-human IgG; 2) anti-mouse IgG; and 3) anti-rabbit IgG, fluorescein conjugated.

Immunoblot Analysis

The proteins were electrophoresed on SDS-PAGE using 10% gels (Laemmli E. K., 1970, *Nature,* 227:680–685). Separated proteins were electroblotted onto nitrocellulose. The membranes were blocked in PBS/0.2% gelatin for 1 hour and incubated overnight at 4° C. with the primary antibody (the optimal dilution for each serum was used). Detection was performed using a peroxidase conjugated secondary antibody (species specific) as described (Sambrook et al, 1989).

Computer Analysis of DNA and Amino Acid Sequence

The blast program (Altschul S. F. et al., 1990, *J. Mol. Biol.,* 215:403–410) at the Genbank database of the National Institutes of Health was used to screen for homologous protein (amino acid sequence set forth in FIGS. 3A and 3B; (SEQ ID NOS:1 and 2)) or DNA (FIG. 4; SEQ ID NOS:3 and 4) sequences.

Results

For purification or molecular cloning of the LC1 antigen a human liver cell line expressing only the latter is suitable; because other autoantibodies are frequently found in patients' sera. Previous work showed that LC1 antibodies react more frequently against human than against rat antigens when tested by immunoblot, although a partial identity between precipitation lines is found when both antigens are tested by immunodiffusion techniques. Human liver cells must therefore be used for the identification of the antigen. These cells express equally well both the LC1 antigen and the cytochrome P450 2D6 which is the LKM1 antigen. The HepG2 cell line, an immortalized human hepatoma cell line, retains many functions of mature human hepatocytes. The P450 2D6,however, is not constitutively expressed in HepG2, as is shown in labeling cells with S35 Cysteine and immunoprecipitating the solubilized cellular proteins with LKM1 antibodies (FIG. 1A). The 48 kDa antigen specifically recognized by LKM1 positive sera is not present in HepG2 cell line. On the other hand, a 62 kDa protein in 10% SDS-PAGE, the expected molecular weight for the LC1 antigen, is immunoprecipitated by LC1 positive serum or LC1 or LC1+/LKM1+ serum (FIG. 1A).

Figure 1B:
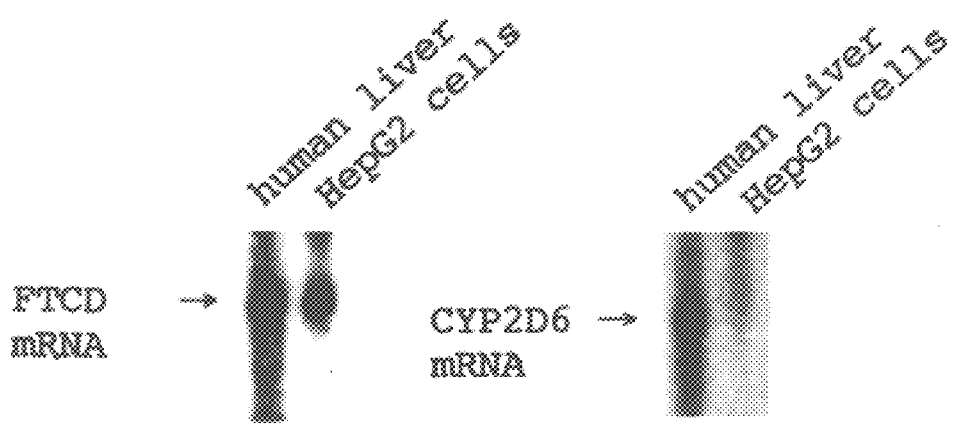

This LC1 positive serum capable of immunoprecipitating only a 62 kDa protein from HepG2 cells was used to screen a cDNA library in the gt11 phage from the same cell line. Six clones were identified yet only two were still positive when the recombinant fusion protein was prepared and tested by immunoblot. The sequence of these two clones overlap and are 85,2% homologous with the already known sequence in the 3' region of the Formiminotransferase-cyclodeaminase (FTCD) from pig liver. A cDNA of 653 bp, the Liver Cytosol Human Clone 1 (LCHCl), was used to establish the relevance of the HepG2 cell line for the detection of LC1 antibodies and the identification of the antigen. Normal human liver and HepG2 cells total RNAs were hybridized using CYP2D6 or FTCD (LCHCl) probes showing that the FTCD mRNA is present in both cell types but that the CYP2D6 mRNA is only present in the former cell type (FIG. 1B). A Northern blot analysis shows that the LC1 antigen (FTCD) mRNA is present in human liver and HepG2 cells, but the LKM1 antigen (P450 2D6) is absent in HepG2 cells, confirming that the HepG2 cell line is a good model for the identification of the LC1 antigen (FIG. 1B).

Figure 2A:
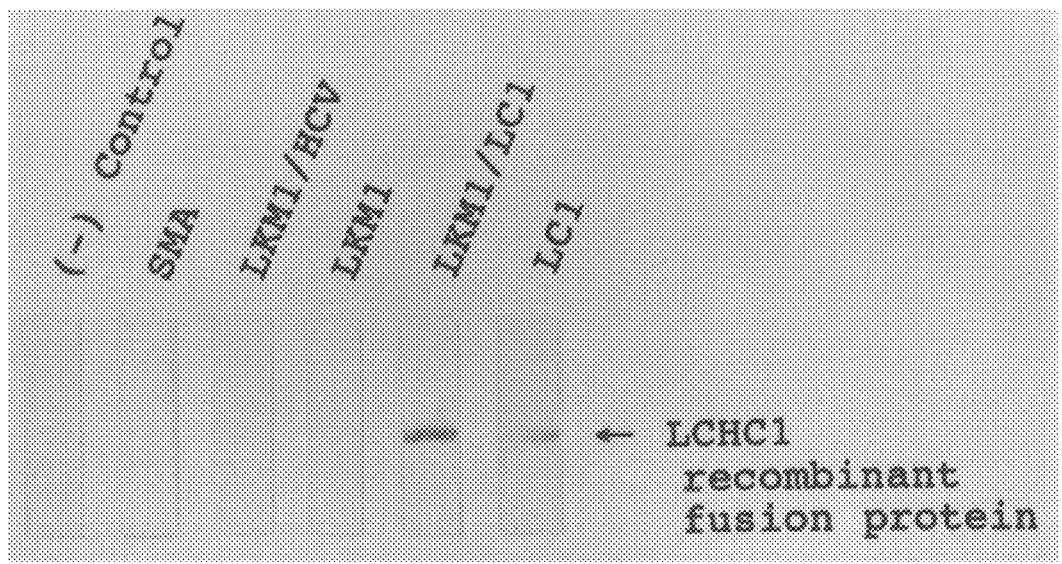
FIGS. 2A and 2B show that the FTCD is the liver specific antigen recognized by LC1 antibodies.

The LCHCl cDNA was subcloned in the pMa1 to allow the preparation of large amounts of the recombinant fusion protein. Forty sera positive for SMA+, LKM1+, LKM1+/LC1+ or LC1+ antibodies and ten sera from normal children were tested by immunoblot against the isolated LCHCl protein. These experiments showed that only the LKM1/LC1 and the LC1 positive sera react with this antigen (FIG. 2A). The LCHCl recombinant fusion protein test by immunoblot, containing the C-terminal region of human FTCD, is recognized only by LC1 positive sera. In total, twenty LC1 positive sera (alone or in association with LKM1 antibodies) recognize the LCHCl recombinant fusion protein (FIG. 2A).

Figure 2B:
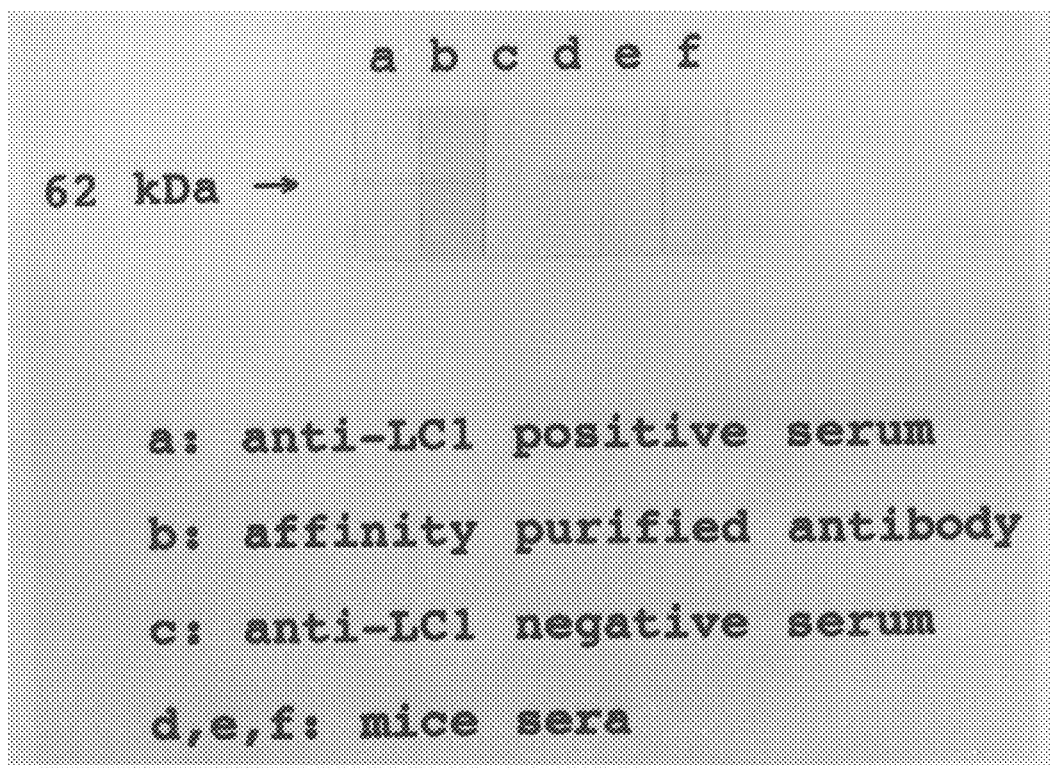
Figure 5A:
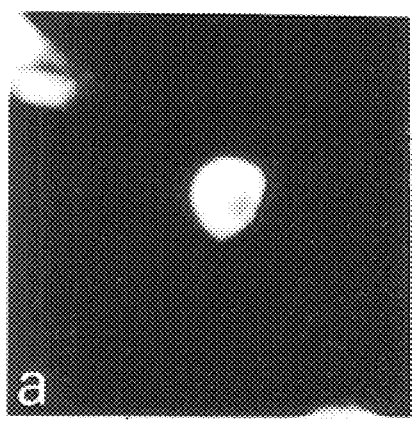
FIGS. 5A–5E illustrate an indirect immunofluorescence of HepG2 cells using a) and b) LC1 positive sera from patients with AIH type II, c) affinity purified antibodies from a patient serum (antibodies were purified from the serum using as an antigen the LCHCl recombinant protein, d) serum from a mouse injected with the LCHCl recombinant protein, e) anti-pig FTCD, and f) anti-nuclear antibody (control)
Figure 5B:
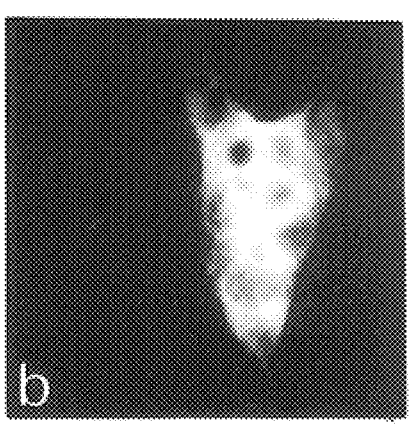
Figure 5C:
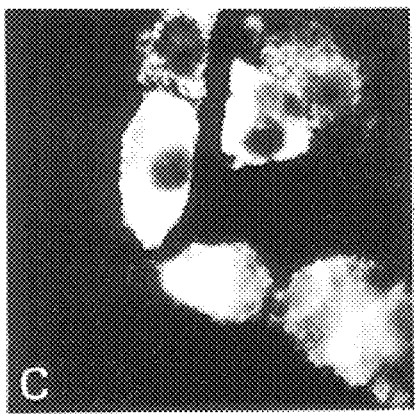
Figure 5D:
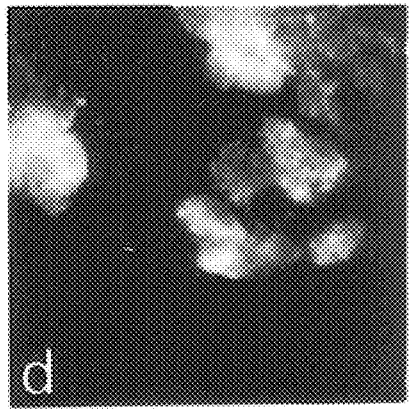
Figure 5E:
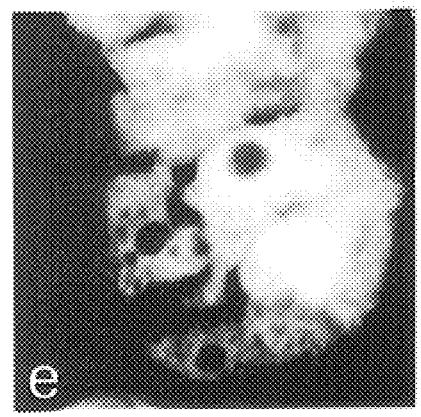
Figure 5F:
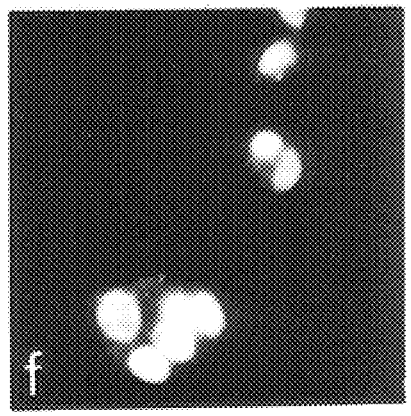

The final step to prove that the FTCD is the LC1 antigen focused on the cross reactivity between the LCHCl recombinant fusion protein and the human liver cytosol 62 kDa protein. LC1 antibodies were affinity purified from one patient serum using the LCHCl protein as an antigen. These antibodies reacted with a 62 kDa human liver cytosol protein when tested by immunoblot (FIG. 2B). The LCHCl recombinant fusion protein was also injected to three C57BL6 female mice. Sera from two out of three immunized mice reacted with the human cytosol 62 kDa protein (FIG. 2B). A cross-reactivity between LCHCl recombinant fusion protein and the human liver cytosol 62 kDa protein is shown. The anti-LCHCl protein affinity purified antibodies (FIG. 2B, line b) as well as the sera from mice immunize with the LCHCl recombinant fusion protein react against a human liver 62 kDa cytosolic protein to an immunoblot assay.

All these results clearly show that the human liver FTCD enzyme is the antigen recognized by LC1 antibodies. Further arguments supporting this conclusion come from previous publications showing that the mature structure LC1 antigen is polymeric with a molecular weight of 240 to 290 kDa (Abuaf et al.). This possible tetrameric structure (each subunit of 62 kDa) was also described as the mature-functional structure of the FTCD (Mackenzie et al., 1980, *J. Biol. Chem.*, 255:9474–9478). This enzyme that was well studied in vitro after its isolation from pig liver, the human liver FTCD's complete sequence is still unknown, is only expressed in hepatocytes and is also the case of the 62 kDa LC1 antigen.

The FTCD is, so far, the only hepatocyte specific autoantigen described in any liver autoimmune disorder. Current work is directed towards the development of specific diagnostic test, easier and faster than those so far used for the detection of LC1 antibodies. One out of ten patients with AIH does not display classical autoantibodies in its serum, a fact that delays detection of a potentially lethal disease. In addition, the characterization of FTCD epitopes as well as a T-cell specific response against this protein have pathogenetic relevance.

The present invention will be more readily understood by referring to the following examples which are given to illustrate the invention rather than to limit its scope.

EXAMPLE I

Western Blot

A human cDNA clone (LKMHC5) was used to lysogenize *E. coli* Y 1089. Total extract or 2 μg of purified fusion protein were electrophoresed on a SDS-polyacrylamide gel of 7.5% and electrically transferred to nitrocellulose paper. The amount of purified fusion protein was established in comparison with known quantities of pure β-galactosidase, by SDS polyacrylamide electrophoresis and Coomassie Blue staining. Two normal human sera, one serum positive for high titers of anti-smooth muscle antibodies from a child with another type of autoimmune hepatitis, four anti-50 kDa positive sera, two anti-66 kDa positive sera, one anti-cytosol positive serum, and affinity purified anti-50 kDa antibody, were used at a dilution of 1:500. A goat antihuman IgG labeled with horseradish peroxydase (Biosys, Compiègne, France) was used at 1:1,000 dilution as second antibody, in all cases. Immunoblots were developed for one minute with 50 mg of diaminobenzidine in 100 ml of Tris-HCl 50 mM, pH 7.4 and $H_2O_2$ at a final concentration of 0.01%.

EXAMPLE II

Elisa

Purified fusion protein from cDNA human clone (LKMHC5) was diluted in Phosphate Buffer Saline pH 7.4 at final protein concentration of 0.2 μg per ml. One hundred μl of this preparation were placed in each U-bottomed well of polyvinyl plates (Greiner, Hergestellt, FRG) and dried at 65° C. overnight. As first antibody, the patients' sera described above for immunoblot analysis were used each at dilutions ranging from 1:100 to 1:12,800. Second antibody was goat anti-human IgG labeled with alkaline phosphatase (Biosys, Compiègne, France) at a 1:1,000 dilution. After washing, one hundred μl of 0.05 M $NaCO_3$ pH 9.8, 0.001 M $MgCl_2$ with 1 mg/ml p.nitrophenylphosphate (Sigma, St. Louis, Mo.) was added to each well. The results were read after 30 minutes at room temperature using a Titertek Multiskan™ (Flow Laboratories, Puteaux, France) at OD 405 nm. Any reading which was less than twice the value obtained for the blank control was considered to be background.

EXAMPLE III

Diagnosis of Autoimmune Hepatitis (AIH)

Fifty sera were collected from patients with autoimmune hepatitis before starting any immunosuppressive treatment. The diagnosis of AIH was made according to criterion defined by the International Autoimmune Hepatitis Group (1). Indirect immunofluorescence was used for the detection of SMA antibodies (FIGS. 5A–5F). Twenty sera positive for SMA (titers >1:100, serum gammaglobulin levels between 19.5–44 g/l). Twenty-three sera were positive for LKM1 by indirect immunofluorescence (titers 1:500 to 1:100,000; serum gammaglobulin levels, 13.5–43 g/l). Twenty-three patients were positive for LC1, sixteen cases in association with LKM1. LC1 positivity was shown by immunodiffusion (titers 1:4 to 1:2048; serum gammaglobulin levels 14.6–35.8 g/l). All positive LC1 reacted with a 62 kDa protein when tested by immunoblot against a human liver cytosol subcellular fraction. Fifteen sera from normal individuals were also used as controls.

The LCHCl recombinant fusion protein was only recognized by LC1 positive patient sera and by the anti-pig FTCD antibody, as shown in FIG. 6.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A DNA sequence set forth in SEQ ID NO:2, wherein said DNA sequence codes for a human liver specific formiminotransferase cyclodeaminase (FTCD) antigen specifically expressed in hepatocytes of patients suffering from an autoimmune hepatitis type II disease.

2. The DNA sequence of claim 1, wherein said antigen has an amino acid sequence as set forth in SEQ ID NO:4.

3. A method of diagnosis of Autoimmune Hepatitis (AIH) type II disease in a patient biological sample, which comprises the steps of:
   a) contacting a human liver specific FTCD antigen encoded by the DNA sequence of claim 2, with said patient biological sample; and
   b) detecting the binding of the antigen to liver cytosol antigen type 1 (LC1) antibodies to form a complex in said sample; whereby the presence of said complex is indicative of AIH type II disease.

4. A method of diagnosis of Autoimmune Hepatitis (AIH) type II disease in a patient biological sample, which comprises the steps of:
   a) contacting a human liver specific FTCD antigen encoded by the DNA sequence of claim 1, with said patient biological sample; and
   b) detecting the binding of the antigen to liver cytosol antigen type 1 (LC1) antibodies to form a complex in said sample; whereby the presence of said complex is indicative of AIH type II disease.

5. An ELISA method of diagnosis of Autoimmune Hepatitis (AIH) type II disease in a patient biological sample, which comprises the steps of:
   a) subjecting an ELISA plate having bound thereto an antigen encoded by the DNA sequence of claim 1 with said patient biological sample; and
   b) detecting the binding of the antigen to liver cytosol antigen type 1 (LC1) antibodies to form a complex in said sample using rabbit anti-human IgG antibodies; whereby the presence of said complex is indicative of AIH type II disease.

* * * * *

SEQUENCE LISTING

```
<160> NUMBER OF SEQ ID NOS: 4

<210> SEQ ID NO 1
<211> LENGTH: 653
<212> TYPE: DNA
<213> ORGANISM: Artificial Sequence
<220> FEATURE:
<223> OTHER INFORMATION: human FTCD antigen

<400> SEQUENCE: 1
ccgcccttcc acgcggcctc agccaagctg acctcgctgg tggacgctga cgcccgggcc    60
```

-continued

```
ttcgaggcct acctgaaagc gatgaagctg cccaaggaca cacccgagga caaggacagg    120
cgtgcggctg ccctgcagga ggggctgagg caggcagtgg ctgtgcccct ggcgctggcg    180
gagacggtgg cctcgctgtg gccggcactg caggagctgg ccctgtgtgg gaacctggcc    240
tgccgatctg acctgcaggt ggcagccaag gccctggaga caggtgtgtt tggtgcctat    300
ttcaacgtgc tcatcaacct gaaagatgtc acggatgacg cgtttaaggc ccaggtccgt    360
cagcgcatct ccagcctcct gcaggaagcc aagacccagg cggcactggt gctggaccgg    420
ctggaggccc ggcaggcgtg acggctggag gggcacctcc ctggaccctg tccttgctga    480
ggcccctcac tgtctggacg acagggtggc ctccagacct gtcctggggg gcccggagag    540
ggcagggagt gggggggcaag gaaggggggg ctctgggggc agtggcatca ccttctgtca    600
cctgtggctt ccagtaaagt gatgacacac caaaaaaaaa aaaaaaaaaa aaa           653
```

<210> SEQ ID NO 2
<211> LENGTH: 660
<212> TYPE: DNA
<213> ORGANISM: Artificial Sequence
<220> FEATURE:
<223> OTHER INFORMATION: human FTCD antigen

<400> SEQUENCE: 2

```
ccgcccttcc gcgaggcttc ggccaagcta accacgctgg tggatgccga cgccgaggcc     60
ttcaccgcct acctggaagc aatgaggctc cccaagaaca cacctgagga aaaggacagg    120
cgcacggcgg ccctacagga gggtctgagg cgggcagtct ctgtgccgct gacgctggcg    180
gagacggtgg cctcgctgtg gccggcgctg caggaactgg cccggtgtgg gaacctggcc    240
tgccggtcag acctccaggt ggcggccaaa gccctggaga tgggcgtgtt tggcgcatat    300
ttcaacgtgc tcatcaacct gagggacatc acagacgagg catttaagga ccagatccac    360
catcgtgttt ccagcctcct gcaggaagcc aagacccagg ctgcactggt gctggactgc    420
ttggagaccc ggcaggagtg acgaaacccc agggacagca ggaccttcga cgctggaagg    480
atagcctcgc ttcccaggtg cagctcccgg caggtctgga cagttccaca gagcacggta    540
ctggccctgt cctcagttcc cgtccaccct tcaaccagtg gctcctggag acttttcctc    600
cctgcctcag ctccctgccc agccagcctc ctgtctccag agaagttctc cattaaaaaa    660
```

<210> SEQ ID NO 3
<211> LENGTH: 146
<212> TYPE: PRT
<213> ORGANISM: Artificial Sequence
<220> FEATURE:
<223> OTHER INFORMATION: human liver specific FTCD antigen

<400> SEQUENCE: 3

```
Pro Pro Phe His Ala Ala Ser Ala Lys Leu Thr Ser Leu Val Asp Ala
 1               5                  10                  15

Asp Ala Arg Ala Phe Glu Ala Tyr Leu Lys Ala Met Lys Leu Pro Lys
                20                  25                  30

Asp Thr Pro Glu Asp Lys Asp Arg Arg Ala Ala Ala Leu Gln Glu Gly
            35                  40                  45

Leu Arg Gln Ala Val Ala Val Pro Leu Ala Leu Ala Glu Thr Val Ala
        50                  55                  60

Ser Leu Trp Pro Ala Leu Gln Glu Leu Ala Leu Cys Gly Asn Leu Ala
65                  70                  75                  80

Cys Arg Ser Asp Leu Gln Val Ala Ala Lys Ala Leu Glu Thr Gly Val
                85                  90                  95
```

-continued

```
Phe Gly Ala Tyr Phe Asn Val Leu Ile Asn Leu Lys Asp Val Thr Asp
            100                 105                 110

Asp Ala Phe Lys Ala Gln Val Arg Gln Arg Ile Ser Ser Leu Leu Gln
        115                 120                 125

Glu Ala Lys Thr Gln Ala Ala Leu Val Leu Asp Arg Leu Glu Ala Arg
        130                 135                 140

Gln Ala
145

<210> SEQ ID NO 4
<211> LENGTH: 146
<212> TYPE: PRT
<213> ORGANISM: Artificial Sequence
<220> FEATURE:
<223> OTHER INFORMATION: human liver specific FTCD antigen

<400> SEQUENCE: 4

Pro Pro Phe Arg Glu Ala Ser Ala Lys Leu Thr Thr Leu Val Asp Ala
1               5                   10                  15

Asp Ala Glu Ala Phe Thr Ala Tyr Leu Glu Ala Met Arg Leu Pro Lys
            20                  25                  30

Asn Thr Pro Glu Glu Lys Asp Arg Arg Thr Ala Ala Leu Gln Glu Gly
        35                  40                  45

Leu Arg Arg Ala Val Ser Val Pro Leu Thr Leu Ala Glu Thr Val Ala
    50                  55                  60

Ser Leu Trp Pro Ala Leu Gln Glu Leu Ala Arg Cys Gly Asn Leu Ala
65                  70                  75                  80

Cys Arg Ser Asp Leu Gln Val Ala Ala Lys Ala Leu Glu Met Gly Val
            85                  90                  95

Phe Gly Ala Tyr Phe Asn Val Leu Ile Asn Leu Arg Asp Ile Thr Asp
            100                 105                 110

Glu Ala Phe Lys Asp Gln Ile His His Arg Val Ser Ser Leu Leu Gln
        115                 120                 125

Glu Ala Lys Thr Gln Ala Ala Leu Val Leu Asp Cys Leu Glu Thr Arg
        130                 135                 140

Gln Glu
145
```